United States Patent
Niehaus (10) Patent No.: US 12,087,031 B2
(45) Date of Patent: Sep. 10, 2024

(54) METHOD AND DEVICE FOR ANALYZING PLANTS

(71) Applicant: SpexAI GmbH, Dresden (DE)

(72) Inventor: Ben Niehaus, Dresden (DE)

(73) Assignee: SPEXAI GMBH, Dresden (DE)

( * ) Notice: Subject to any disclaimer, the term of this patent is extended or adjusted under 35 U.S.C. 154(b) by 332 days.

(21) Appl. No.: 17/426,427

(22) PCT Filed: Feb. 5, 2020

(86) PCT No.: PCT/EP2020/052840
§ 371 (c)(1),
(2) Date: Jul. 28, 2021

(87) PCT Pub. No.: WO2020/161176
PCT Pub. Date: Aug. 13, 2020

(65) Prior Publication Data
US 2022/0108543 A1 Apr. 7, 2022

(30) Foreign Application Priority Data
Feb. 6, 2019 (EP) ...................... 19155791

(51) Int. Cl.
*G06V 10/58* (2022.01)
*G06N 3/08* (2023.01)
(Continued)

(52) U.S. Cl.
CPC ............... *G06V 10/58* (2022.01); *G06N 3/08* (2013.01); *G06V 10/141* (2022.01); *G06V 10/147* (2022.01); *G06V 20/188* (2022.01)

(58) Field of Classification Search
CPC .... G06V 20/188; G06V 10/41; G06V 10/147; G06T 7/0002; G06T 2207/10036; G06T 2207/30188; G06N 3/08
See application file for complete search history.

(56) References Cited

U.S. PATENT DOCUMENTS 10,458,908 B2 10/2019 Yarden et al.
10,761,075 B2 * 9/2020 Gui .................... G01N 33/0098
(Continued)

FOREIGN PATENT DOCUMENTS

DE 102006043117 B3 4/2008
DE 102009055626 A1 5/2011
(Continued)

OTHER PUBLICATIONS

Chunjiang, et al. (Computer English Translation of Chinese Patent No. CN108830792 A), pp. 1-10. (Year: 2018).*
(Continued)

*Primary Examiner* — Daniel G Mariam
(74) *Attorney, Agent, or Firm* — The Webb Law Firm (57) ABSTRACT

The disclosure relates to a method for analyzing a plant, in particular for analyzing cannabis, using an illumination unit, a sensor unit, and an analysis unit, said analysis unit having a data-based classifier. The disclosure additionally relates to a device for analyzing a plant, said device comprising an illumination unit for lighting the plant to be analyzed and a sensor unit for receiving analysis input data, wherein the analysis input data contains at least spectral information, in particular an absorption spectrum or a reflection spectrum of the training plant. The device additionally comprises an analysis unit for analyzing the received analysis input data and for determining at least one property of the plant to be analyzed. The analysis unit is also designed to determine at least one property of the plant using a data-based classifier and the previously received analysis input data.

7 Claims, 4 Drawing Sheets

(51) Int. Cl.
*G06V 10/141* (2022.01)
*G06V 10/147* (2022.01)
*G06V 20/10* (2022.01)

(56) References Cited

U.S. PATENT DOCUMENTS

| | | | | |
|---|---|---|---|---|
| 2010/0039804 | A1* | 2/2010 | Budde | H05B 45/22 |
| | | | | 356/402 |
| 2016/0349180 | A1 | 12/2016 | Tischler et al. | |
| 2017/0032258 | A1* | 2/2017 | Miresmailli | G05B 15/02 |
| 2019/0033210 | A1* | 1/2019 | Yarden | B07C 5/342 |

FOREIGN PATENT DOCUMENTS

| | | |
|---|---|---|
| DE | 102010027144 A1 | 1/2012 |
| WO | 2007041755 A1 | 4/2007 |
| WO | 2017134669 A1 | 8/2017 |

OTHER PUBLICATIONS

Ralph (Computer English Translation of European/German Patent No. DE102009055626 A1), pp. 1-9. (Year: 2011).*
Li, et al. (Computer English Translation of Chinese Patent No. CN 207399330 A1), pp. 1-11. (Year: 2018).*
Tek, et al. (Computer English Translation of WO 2016/186238 A1), pp. 1-11, (Year: 2016).*
Goel et al., "HyperCam: Hyperspectral Imaging for Ubiquitous Computing Applications", UBICOMP '15, Sep. 7-11, 2015, pp. 145-156, Osaka, Japan.

* cited by examiner

METHOD AND DEVICE FOR ANALYZING PLANTS

CROSS-REFERENCE TO RELATED APPLICATIONS

This application is the United States national phase of International Application No. PCT/EP2020/052840 filed Feb. 5, 2020, and claims priority to European Patent Application No. 19155791.7 filed Feb. 6, 2019, the disclosures of which are hereby incorporated by reference in their entirety.

BACKGROUND OF THE DISCLOSURE

Field of the Disclosure

The disclosure relates to a method and a device for analyzing plants. The disclosure relates in particular to an automated optical method for analyzing plants and for evaluating properties of plants, in particular in the context of cannabis.

Description of Related Art

Even today, the evaluation of growth conditions of plants, both in the field and in the greenhouse, is a task largely performed by the human eye. However, such a "manual" analysis and evaluation of plant properties is time-consuming, costly and inaccurate.

In cultivating plants, in particular the health or a possible disease infestation, as well as the stressors are of particular importance. If a plant is infested by insects, fungi or viruses, both the quality and the quantity will suffer at the next harvest. However, a disease infestation is often visible to the human eye only very late.

Further properties of plants, such as for example the water content or the THC content of cannabis, are particularly difficult to assess by manual analysis.

Some methods for an improved analysis of plant properties are already known from the prior art. Specifically, document WO 2017/134669 A1 discloses a device and a corresponding method for analyzing plants. The device described comprises an optical monitoring unit configured to acquire image data and spectral data about a plant. Thereafter, a control unit calculates structural parameter from the image data. Depending on the ratio between the calculated structural parameters and the spectral data, conclusions are made in view of a quality property of the plant.

SUMMARY OF THE DISCLOSURE

It is an object of the present disclosure to provide a method and a device which allow for an analysis of the properties of a plant, in particular the properties of cannabis, already at an early stage, so as to be able to make reliable statements on the growth conditions to be expected in the future.

To achieve the above-mentioned object, a method for analyzing a plant, in particular for analyzing cannabis, with the use of an illumination unit, a sensor unit and an evaluation unit is provided, wherein the evaluation unit comprises a data-based classifier and the method comprises the following steps:

training the classifier, the training comprising the following steps:
lighting a training plant having at least one known property using the illumination unit;
acquiring training input data by measuring the radiation reflected from the training plant;
training the classifier with the acquired training input data, as well as training output data, wherein the training input data at least comprise spectral information, in particular an absorption spectrum or a reflection spectrum of the training plant, and the trainings output data are associated to the training input data and comprise information about at least one property of the training plant;
acquiring analysis input data by means of the sensor unit, the acquisition comprising the following steps:
illuminating a plant to be analyzed which has at least one unknown property, using the illumination unit;
acquiring analysis input data by measuring the radiation reflected from the plant to be analyzed;
determining a property of the plant to be analyzed, using the classifier previously trained with the training input data and the trainings output data and the acquired analysis input data.

An illumination unit of the method according to the present disclosure may in particular comprise one or a plurality of LEDs which, in dependence on the concrete embodiment, may be of a broadband or a narrowband design. The sensor unit used may in particular comprise a camera. Further, as will be described hereinafter in more detail in the context of the device according to the present disclosure, the sensor unit may comprise a spectrometer. The evaluation unit may in particular include a processor and a memory.

The spectral information may in particular include a complete spectrum (for example an absorption spectrum or a reflection spectrum). As an alternative, it may be provided that the spectral information only comprise information extracted from an acquired spectrum. For example, the spectral information may only include information about an absorption maximum or an absorption minimum, e.g., a wavelength and/or an intensity that describe an absorption maximum or an absorption minimum.

While the classifier is trained, it "learns" how to correlate the input data with the output data. For this purpose, a training data set is used that comprises training input data and training output data. This training data set is obtained by using training plants having at least one known property (e.g., with respect to the plant variety) and by lighting them in advance with the illumination unit, so that the training input data (e.g., a reflection spectrum) subsequently acquired and the known training output data (e.g., describing the water content of a plant) can be correlated with each other. Here, the training output data comprise information about at least one property of the training plant. This property may in particular be the disease or health state or the plant variety. In addition, the training output data may include information about further properties of the plant, in particular about specific ingredients of a plant (e.g., the THC content of cannabis) or about abiotic factors of a plant. The abiotic factors comprise, for example, the nutrient content of the plant and its distribution in the plant, macro-nutrients (in particular nitrogen, phosphor, potassium, calcium, sulfur, magnesium, carbon, oxygen, hydrogen), micro-nutrients (in particular vitamins, minerals, bulk elements and trace elements) and secondary plant substances (such as, for example, iron, boron, chloride, manganese, zinc, copper, molybdenum and nickel), and the water content of the plant.

Further, the output data may comprise information about the biotic stress factors, this includes in particular the infestation of a plant by insects, viruses and mildew.

All above-mentioned properties of a plant which are used for the training of the classifier can afterwards be determined by the classifier in an analysis process.

Regarding the above-mentioned properties of a plant, it may be provided according to the method of the present disclosure that the current properties of a plant are determined by the classifier. It may also be provided that future properties of a plant can be determined by the classifier. Thereby, it is possible to make predictions in particular about the further development of the growth process of a plant, which allow for better predictions about the future growth process and to influence the same by possible measures, if necessary. If, for example, the method according to the present disclosure detects that the water content of a plant is too low, it can conclude that the future growth will develop in a suboptimal manner, so that the watering of the plant may be adjusted as a counter-measure. Further, in reaction to a negative prognosis, an alarm signal may be issued and, for example, the lighting settings may be adjusted as a counter-measure, so that the plant may enjoy optimized lighting conditions, whereby the future growth process can be influenced positively.

According to one embodiment of the method of the present disclosure it may be provided that the method of the present disclosure is configured to make a prediction about the development of the cannabinoid content over the future development time of the plant. Cannabinoids may in particular be THC(A), CBD(A), CBN, CBG, THCV, CBDV. It may further be provided that the method of the present disclosure is configured to determine the terpene content over the future development time of the plant. Terpenes may in particular be PNE, MYR, LME, CYE, LNL, HUM, OCM or TPW.

The method of the present disclosure aims at providing a fully automated method which allows for an analysis of the plant properties that is as precise as possible. Thereby, the growth process of the plants can be better analyzed, predicted and influenced. It can be expected that the method of the present disclosure can make a major contribution to increasing the efficiency of plant cultivation.

Although reference is frequently made to a "plant" in the context of the disclosure, it is obvious to a skilled person that this does not necessarily refer to the entire plant, but may also refer to plant parts, in particular plant stems or plant leaves.

According to one embodiment of the present disclosure it may be provided that also a plurality of properties of a plant can be determined. For example, it may be provided that both the health state and the water content of a plant is determined. For this purpose, either a single classifier may be used, which performs a determination of a plurality of properties, or a combination of several classifiers may be used which are particularly suited for the determination of one specific property, respectively.

After the classifier has been trained, plants having at least one unknown property can be examined using the illumination unit, the sensor unit and the evaluation unit.

Although the training of the classifier for "a plant" is described above, it is preferred to use a plurality of plants so that the training data set comprises as much information as possible. Generally, it applies that the accuracy of the classifier increases, if as many data as possible is available during training. For example, it may be provided that the step of training the classifier with a plurality of plants is repeated in succession until the classifier is sufficiently accurate. For determining the detection accuracy or rate of the classifier, test plants may be used, for example, the properties of which are known and which are examined using the trained classifier. Since the properties of the test plants are known, it can be determined after the examination how many times the assessment by the classifier was correct and how high the detection rate of the classifier is. If the detection rate is below a required detection rate, e.g., below 90% or 95%, the classifier can be trained with further training plants until a sufficiently high detection rate is achieved.

According to an embodiment of the method of the disclosure it may be provided that the training input data comprise no image data. Further, it may be provided that the training input data exclusively comprise spectral information.

According to one embodiment of the method of the present disclosure it may be provided that for increasing the accuracy of the method, the training input data and the analysis input data additionally include images of the training plant and of the plant to be analyzed. In other words: it may be provided that the training input data additionally includes images of the training plant and the analysis input data additionally includes images of the plant to be analyzed. By providing additional information correlating with the current and/or future plant properties, the detection rate of the classifier can be increased. In addition, providing the images allows for the detection of additional properties which may possibly not be detectable. If spectral information was used exclusively.

According to another embodiment of the present disclosure it may be provided that, independently of spectral information, the training input data and the analysis input data includes images of the training plant and the plant to be analyzed. In other words: according to this embodiment, it is not absolutely necessary that the input data includes spectral information.

According to another embodiment of the method of the present disclosure it may be provided that the training the classifier additionally comprises the following steps:

providing images as training input data which are to be used for training the classifier, and training output data associated to the images provided;

rotating the images provided;

associating the training output data, which are associated to the initially provided images, to the rotated images;

combining the initially provided images and the rotated images, as well as the training output data associated to the images into an extended training data set; and training the classifier with the use of the extended training data set.

As already explained above, the detection rate of the classifier is generally higher if particularly comprehensive training data is available. For an increase in the accuracy of the classifier, the training data set may preferably be extended in an "artificial" manner. If, for example, the training data set includes only ten images of training plants, it is possible by the above measure to generate, for example, 100 additional images for each of the images, in which the initially provided image is incrementally rotated, respectively. In rotating the images, it may be provided in particular that the initially provided images are rotated about an axis of rotation that is perpendicular to the image plane. In this manner, the extension of the data set can be made without any change to the test stand. In this context, one may speak of a "software-based extension" of the training data set.

As an alternative, it may be provided that already during the acquisition of the training input data or the images, either the plant or the camera is rotated or swiveled so as to obtain images in different perspectives. The training data set can be extended in this manner as well, without having to provide additional test plants. Here, it may be provided in addition that either the camera used for capturing the images or the training plant is swiveled or rotated automatically, so as to thereby automatically generate an extended training data set. Here, it may be provided in particular that the camera is movable along a circular path and is also swivel-mounted, and that images of the training plant are captured at defined intervals. In this context, one may thus speak of a "hardware-based extension" of the training data set.

In extending the training data set, it may be provided, for example, that initially an extended data set is created and stored (for example, on a hard disk), before the training process with the extended data set is started. As an alternative, it may also be provided that the extended data set is not stored (permanently), but that the extended data generated are immediately used to train the classifier. In this manner, the classifier can be trained with the new data directly after a new image has been generated, without having to store these data. This may be advantageous if, during the extension of the training data set, a particularly large amount of data is expected, while at the same time the available memory space is limited.

The extended training data set thus comprises the initially provided images (training input data) and the training output data associated to these images on the one hand, as well as, on the other hand, the "manipulated" images to which the same training output data is associated as is associated to the initially provided images.

According to another embodiment of the present method, it may be provided that the training data set is extended by mirroring the initially provided images. Here, it may be provided that the images are mirrored around a horizontal or a vertical axis.

It may further be provided that an essential or characteristic element of the images, e.g., a plant leaf, is shifted within the image. For example, in an initially provided image, a plant leaf captured may be located in a bottom left part of the image. For an extension of the training data set, the plant leaf can be shifted to various positions in the image, e.g., to the center of the image or to the top right part of the image.

According to another advantageous embodiment of the disclosure it may be provided that, for extending the training data set, an essential or characteristic element of the images is scaled. To this end, it may be provided on the one hand that the distance between a camera and the object to be captured (for example, the plant or a plant leaf) varies while capturing the images. As an alternative, it may also be provided that the distance between the camera and the object to be captured remains constant, with the scaling effect being obtained through a zoom function of the camera. In both cases described above, one may also speak of a "hardware-based scaling". It may further be provided that the images available include a characteristic element that is digitally processed after the images have been captured. In this context, one may speak of a "software-based scaling".

According to another alternative embodiment of the method of the present disclosure, it may be provided that the brightness of the image is varied for an extension of the training data set. To this end, the illumination unit may be adjusted already during the image capturing such that the plant to be analyzed is illuminated with different intensities. Thus, various images under different lighting conditions can be captured by the sensor unit, in particular by a camera. As an alternative hereto, it may be provided that the images are illuminated under the same conditions and the brightness is digitally post-processed thereafter. Digital post-processing has the advantage that a comprehensive training data set can be compiled with relatively little effort.

It may also be provided that for the extension of the training data set, the images are superimposed with a noise signal. The noised signal may, for example, be white noise.

According to a particularly preferred embodiment of the method of the present disclosure it may be provided that for increasing the accuracy of the method, the training input data and the analysis input data additionally include genetic information about plants. Thereby, the reliability and the precision of the classifier can be increased by providing additional information about the DNA of a plant during the training stage. Taking the genetic information into account can particularly increase the precision of the classifier, since many properties of plants, such as, among others, resistance against bacteria, viruses and other diseases and the sensitivity to temperature or humidity variations, depend largely on the predisposition of the plant. Taking genetic information into account is advantageous in particular in the case of cannabis. One reason is that cannabis is generally cultivated in greenhouses and climate chambers, wherein, as a rule, a plurality of plants are present which are genetically identical. If the genetic information about the plant cultivated is known and the training data set used in training the classifier also included plants having the same DNA, taking genetic information into account results in a significant improvement of the method of the present disclosure. Generally, in the above described scenario including genetically identical plants, it is not necessary to determine the genetic information of the plant to be analyzed again every time. Rather, it may be provided that the corresponding type of the plant and, corresponding to the selection, the genetic information of the plant to be analyzed are read from a predetermined list as a part of the analysis input data and are transmitted to the classifier. The genetic information may, for example, use the entire DNA information or only individual DNA sequences which are connected to a specific property. For example, certain DNA sequences may correlate with a high resistance against certain pathogens.

Further, according to an embodiment of the method of the present disclosure, it may be provided that the classifier is based on an artificial neural network, in particular a Convolutional Neural Network (CNN). First studies have already shown that in the context of the method of the present disclosure, neural networks, in particular so-called Convolutional Neural Networks lead to high detection rates are thus particularly suitable. CNNs are predestined in particular in connection with multidimensional data and are therefore particularly useful in combination with the method of the present disclosure.

It may also be provided that the classifier is based on one of the following methods: Recurrent Neural Network (RNN), Long Short-Term Memory (also referred to as LSTM), Supervised Learning, Unsupervised Learning and Machine Learning. It may further be provided that the classifier is based on a combination of a plurality of the previously mentioned methods.

According to an embodiment of the method of the present disclosure, it may be provided that for an increase in the accuracy of the method while training the classifier, the training input data and the analysis input data include information about the temporal change of the input data acquired. This may increase the accuracy of the analysis even further, as will be described in the following. In certain situations, it may be difficult for the classifier to detect the property of a plant, e.g., the health state and the state of disease. This is due to the fact that the currently measured values as such may be within an acceptable and tolerated range, while, however, showing an abrupt temporal change. For example, a measured absorption peak (or the wavelength and the intensity of a measured absorption peak) is in a range that is typically associated to a healthy plant. Nevertheless, the temporal change of the measured absorption peak can provide an indication that the plant is already infested by a pathogen. Therefore, taking into account the information about the temporal change of the measuring data acquired, can result in a significant improvement of the method of the present disclosure. In particular, diseases and other problems in the growth of a plant can be detected, which would otherwise only be difficult to detect. Here, it may be provided, for example, that the training input data include data which represent the temporal difference of the measuring data acquired. To this end, it is possible, for example, to calculate the difference between an absorption spectrum acquired at a time t and an absorption spectrum acquired at a time t-n, and the classifier can be trained with data corresponding to the difference between both spectra. It may further be provided that not the entire spectra are subtracted from each other, but only one feature or a plurality of features extracted from the spectra acquired. For example, the position (or the wavelength) of an absorption peak at the time t may be compared to the position (or the wavelength) of an absorption peak at the time t-n and the difference may be calculated therefrom. Thereby, a temporal "surge" of an absorption peak can be detected, which may, for example, be related to the disease of a plant.

According to a further preferred embodiment of the method of the present disclosure, it may be provided that for improving the classifier, training data are used that comprise environmental data. Environmental data include in particular air and/or ground temperature, atmospheric pressure, nutrient supply of the plant (through water, ground and/or nutrient medium), light conditions (both in a greenhouse and in the open air) and weather information (e.g., sunny, cloudy, rainy and/or windy). In the environmental data, in particular current data, data of the past and/or future data may be taken into consideration in order to ensure as accurate an analysis as possible of the current or also the future properties of the plant. The future data may include in particular information about a weather forecast.

According to an embodiment of the method of the present disclosure, it may also be provided that the steps of lighting a training plant having at least one known property using the illumination unit and of acquiring training input data by measuring the radiation reflected from the training plant include the following steps:

illuminating the training plant using a first light source having a first emission spectrum;
 acquiring training input data by measuring the radiation reflected from the training plant;
 illuminating the training plant using a second light source having a second emission spectrum; and
 acquiring training input data by measuring the radiation reflected from the training plant.

It may further be provided that the steps of lighting a plant to be analyzed having at least one unknown property using the illumination unit and of acquiring analysis input data by measuring the radiation reflected from the plant to be analyzed include the following steps:

illuminating the plant to be analyzed using a first light source having a first emission spectrum;
 acquiring training input data by measuring the radiation reflected from the training plant;
 illuminating the training plant using a second light source having a second emission spectrum; and
 acquiring training input data by measuring the radiation reflected from the training plant.

This preferred embodiment offers the advantage that spectral information about the training plant and the plant to be analyzed can be acquired in a simple and economic manner. Instead of providing a relatively complex and costly spectrometer, the preferred embodiment of the present disclosure makes it possible to provide a plurality of LEDs with different emission spectra, as well as a camera (e.g., a CCD or CMOS camera) to capture the spectral information. Different from a conventional spectrometer, additional prisms and/or optical gratings are not necessarily needed according to the preferred embodiment. Studies on which the present disclosure is based, have shown that the spectral information provided in this manner are useful in concluding on the above described properties of a plant. In other words: the studies conducted could show a high correlation between the spectral information provided according to the preferred embodiment and the plant properties. The first emission spectrum and the second emission spectrum may in particular have central wavelengths which are spaced apart by at least 50 nm, preferably at least 100 nm, particularly preferred at least 150 nm and in particular 200 nm. The camera used may preferably be a grayscale camera. As an alternative, it is also possible to use a camera having a color sensor. The above described steps of lighting the plants and acquiring the input data may be implemented in particular as successive method steps, wherein the four steps may be implemented during the training and the four steps during the analysis may be implemented as four successive steps, respectively. In analogy, it may further be provided that also a third and a fourth light source are used which have a third and a fourth emission spectrum.

Furthermore, for achieving the above-mentioned object, a device for analyzing a plant, in particular a hemp plant, is provided, which comprises the following:

an illumination unit for lighting the plant to be analyzed;
 a sensor unit for acquiring analysis input data, wherein the analysis input data include at least spectral information, in particular an absorption spectrum or a reflection spectrum of the training plant; and
 an evaluation unit for evaluating the analysis input data acquired and for determining at least one property of the plant to be analyzed; wherein
 the evaluation unit is configured to determine the at least one property of the plant using a data-based classifier, as well as the previously acquired analysis input data.

The illumination unit may in particular comprise one or a plurality of LEDs. It is a particular advantage of LEDs that they are easy to control, available at low prices and available in a large number of different properties (in particular different emission spectra). For example, it may be provided that the illumination unit comprises a plurality of LEDs, each with a different emission spectrum. Here, the individual LEDs may include narrowband emission spectra. The emission spectra of the individual LEDs may overall extend over the UV range, the visible and the infrared range, For example, a total of 12 LEDs, each with narrowband emission spectra can be used, the overall emission spectrum of the LEDs comprising a wavelength range of 290 to 950 nm. As an alternative, it may be provided that the illumination unit has a broadband light source, in particular a broadband LED.

The sensor unit is configured to acquire spectral information about the plant to be analyzed. For example, a spectrometer may be provided for this purpose. However, the use of a "conventional" spectrometer is not necessarily required. While a conventional spectrometer allows for a direct measuring of a spectrum (in particular of an absorption or a reflection spectrum), there are alternative possibilities to (indirectly) acquire spectral information without a conventional spectrometer.

According to a further preferred embodiment of the disclosure it may be provided that the illumination unit comprises at least two light sources with different emission spectra. It may be provided, for example, that the illumination unit has a plurality of LEDs with emission spectra having central emission wavelengths which are spaced apart by at least 50 nm, preferably at least 100 nm, particularly preferred at least 150 nm and in particular 200 nm. In particular, it may be provided that the illumination unit comprises a plurality of LEDs with different emission spectra. By using a plurality of LEDs with different emission spectra, it may be achieved that the plant to be analyzed is successively illuminated by different LEDs and the sensor unit can thereafter acquire and analyze the light reflected from the plant. This may be particularly advantageous, since an analysis device that is economic and easy to implement can be provided in this manner.

According to a further embodiment of the analysis device of the present disclosure, it may, e.g., be provided that the sensor unit merely comprises a camera. To this end, the illumination unit may, for example, comprise 10 LEDs each having a narrowband emission spectrum, each with a different central wavelength. The central wavelength of the LEDs may each be apart by, e.g., approximately 100 nm, so that the overall emission spectrum of all LEDs can comprise approximately 1000 nm. For acquiring the spectral information, it may be provided according to an embodiment of the device of the present disclosure that the plant to be analyzed is lighted with a first LED and the light reflected from the plant is acquired by a camera. Thereafter, the plant to be analyzed can be lighted using a second LED (having an emission spectrum different from the first LED) and the light emitted from the plant can be acquired again. This procedure can be repeated until an image has been captured by the camera for all of the ten LEDs. Thereafter, the data of the camera can be evaluated. In particular, it may be provided that the camera acquires an RGB signal for each pixel. Therefore, the light intensity of the individual RGB sub-pixels can be used to gain information about the reflection spectrum which is dependent on the LED used. In this manner, spectral information can be acquired without using a "conventional" spectrometer. In this manner, the plant to be analyzed can thus be illuminated successively in a narrowband fashion and the measured spectrum can be acquired in a broadband fashion. This structure allows for a very economic and quick analysis of the plants. In other words: a spectrum is "scanned" in this manner.

The evaluation unit of the analysis device of the present disclosure may in particular include a memory for storing the training and/or analysis data, as well as a processor for performing the above-described method of the present disclosure.

Regarding the classifier used in the context of the analysis device of the present disclosure, it is in particular possible to use one of the classifiers or classification methods described above in the context of the method of the present disclosure.

According to a preferred embodiment of the present disclosure, it may be provided that the sensor unit comprises a spectrometer. Using a spectrometer allows for the acquisition of high-resolution spectral information. Using high-resolution spectral information while training the classifier, it is made possible to increase the accuracy and the reliability of the classifier.

According to a particularly preferred embodiment of the device of the present disclosure it can be provided that the sensor unit comprises a camera, in particular a CMOS camera, having a sensor surface. In particular, it may be provided that the camera used has a special anti-reflection layer so as to acquire as strong a signal as possible and to allow for an enhanced signal-to-noise ratio (SNR) and to thereby increase the accuracy and the reliability of the classifier.

Further, it may be provided that the camera of the analysis device of the present disclosure is configured as a 3D camera, in particular a stereoscope camera. The use of a 3D camera allows in particular to gather information about the volume of a plant. To this end, for example, a plant leaf can be placed on a planar support and the contour of the leaf can be captured by the 3D camera. From the data acquired, the volume of the leaf can thereafter be calculated directly. In this context, it may be provided, for example, that the device of the present disclosure is used to determine the THC concentration of cannabis leaves to be analyzed. Through the use of the 3D camera and the possibility to determine a volume, it then becomes possible to determine not only the THC concentration, but also the absolute amount of THC. The same can thus be determined by a simple multiplication of the THC concentration and the volume of the plant leaf. Thus, it can be determined in a simple manner how much THC a cannabis leaf or an entire batch of plants contains.

Another advantage of the use of a 3D camera can be seen in the fact that it allows to determine the arrangement of the plant and the camera (relative to each other). Thereby, the angle of reflection of the light reflected from the plant can be calculated, wherein this angle of reflection can be incorporated into the training input data, as well as into the analysis input data.

According to a preferred embodiment of the present disclosure, it may be provided that a plurality of 3D cameras is used which capture the plant to be examined from different directions. Thereby, it becomes possible to determine the volume of a plant or a leaf as accurately as possible. Consequently, the determination of the absolute THC content can thus be made in a particularly accurate manner.

According to an embodiment of the present disclosure it may be provided that a stereoscopic camera is used. As an alternative, it may be provided that a method based on structured light is used to determine the three-dimensional shape or to determine the volume of the plant to be examined.

It may further be provided that the illumination unit of the device of the present disclosure comprises at least two lighting elements, in particular at least two LEDs. These may in particular show different emission spectra. According to a preferred embodiment it may be provided that a plurality of LEDs, e.g., ten or 20 LEDs with different emission spectra are used. Using a plurality of LEDs with different emission wavelengths is advantageous in particular if the device of the present disclosure uses no conventional spectrometer, but the spectral information about a plant are "scanned" by the individual LEDs (as explained above).

In addition, it may be provided that the lighting elements of the device of the present disclosure are arranged on a circular path that surrounds the sensor surface of the camera. Thereby, a particularly homogeneous illumination of the plant to be examined can be ensured. Another advantage of arranging the lighting elements on a circular path surrounding the sensor surface of the camera is that the homogeneous illumination of the plant to be analyzed possible irregularities during the acquisition of the training and analysis input data are reduced. This has a positive effect on the detection rate of the classifier.

It may also be provided that the sensor unit and/or the illumination unit of the device of the present disclosure comprise a cooling element. Using a cooling element, it is possible in particular to reduce the noise of the sensor unit and/or the illumination unit. Thereby, the accuracy and the reliability of the classifier can be improved. For example, it may be provided that the cooling element is designed as a Peltier element or comprises a Peltier element.

According to one embodiment of the device of the present disclosure it may be provided that the cooling unit comprises a control unit which cools the sensor unit and/or the illumination unit or at least one element of the sensor unit and/or the illumination unit to a predeterminable temperature.

According to a further embodiment of the analysis device of the present disclosure it may be provided that the sensor unit additionally comprises a temperature sensor and/or a humidity sensor. It may also be provided that the sensor unit additionally acquires data regarding the weather forecast.

According to one embodiment of the analysis device of the present disclosure it may further be provided that the temperature sensor comprises a thermal imaging camera.

It may further be provided that the sensor unit of the present disclosure comprises a sensor surface provided with a UV/VIS-conversion coating. Here, the sensor surface may in particular be the sensor surface of a camera. By using a UV/VIS-conversion coating, the sensitivity of the sensor unit, in particular of the camera, in the UV range can be increased. This is advantageous in particular because commercially available CCD and CMOS cameras typically have a very low luminous efficiency in the UV range. According to the preferred embodiment of the device of the present disclosure it may therefore be provided that the sensor surface is provided with a thin layer of a material that absorbs UV light and subsequently emits visible light. In particular, it may be provided that the sensor surface provided with a thin layer of 1-naphthalene carboxaldehyde, 2-hydroxy-,[(2-hydroxy-1-naphthalenyl)methylene]hydrazone(9CI]. This layer may in particular be deposited on the sensor surface by means of physical vapor deposition (PVD). By using the UV/VIS coating, the detection rate of the classifier can be increased significantly.

For the sake of completeness, the method of the present disclosure has been described above in the context of the training process and the analysis process. It is regarded as obvious that the process of training does not necessarily have to be performed at the user end, but that a provider of the method of the present disclosure, as well as the device of the present disclosure can take over the complete training process so that the user can use the method of the present disclosure or the device of the present disclosure without prior training. Therefore, for achieving the above-mentioned object, a further embodiment of the present disclosure provides a method for analyzing a plant, in particular for analyzing cannabis, using an illumination unit, a sensor unit and an evaluation unit, wherein the evaluation unit comprises a data-based classifier and the method comprises the following steps:

illuminating a plant to be analyzed having at least one unknown property using the illumination unit;

acquiring analysis input data by measuring the radiation reflected from the plant to be analyzed, using a sensor unit; wherein the analysis data at least include spectral information, in particular an absorption spectrum or a reflection spectrum of the plant to be analyzed;

determining a property of the plant to be analyzed, using a classifier, which has previously been trained with training input data and training output data, and the analysis input data acquired, wherein the training output data are associated to the training input data and include information about at least one property of the training plant.

Furthermore, it is regarded as obvious that the above described method for analyzing a plant, which includes no training process, is also compatible and combinable with all embodiments described above in combination with the training process.

Moreover, it is regarded as obvious that all steps of the method of the present disclosure explained above can be combined with the device of the present disclosure and, conversely, all embodiments of the device of the present disclosure can be combined with the method of the present disclosure.

BRIEF DESCRIPTION OF THE DRAWINGS

The disclosure will be described in the following in more detail with reference to the embodiments and the drawings. Specifically, the drawings show the following

DETAILED DESCRIPTION

Figure 1:
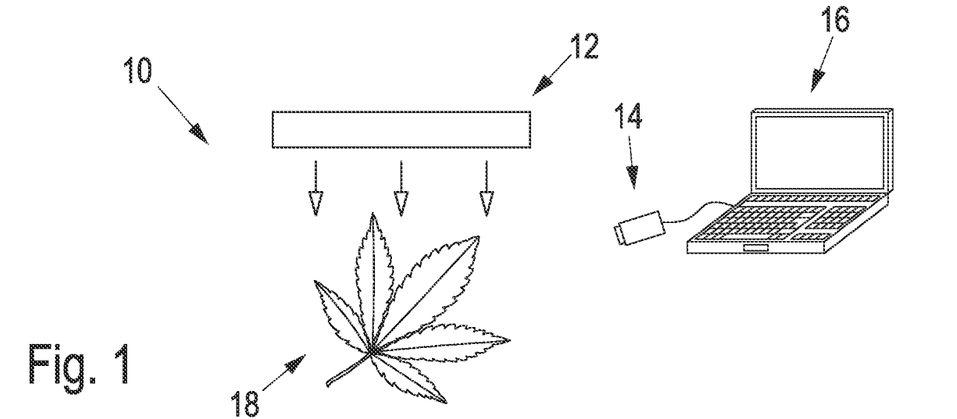
FIG. 1 is a schematic diagram of a first embodiment of the disclosure.

FIG. 1 shows a first embodiment of the analysis device 10 of the present disclosure. The analysis device 10 comprises an illumination unit 12, a sensor unit 14, as well as an evaluation unit 16. The sensor unit 14 may, for example, be designed as a camera or a spectrometer. In the embodiment illustrated, the evaluation unit 16 is designed as a portable computer. The analysis device 10 is configured to analyze a plant (or a plant leaf) 18. To this end, the plant 18 is irradiated by the illumination unit 12. The radiation reflected from the plant 18 is subsequently captured by the sensor unit 14. The data acquired by the sensor unit 14 are evaluated by the evaluation unit 16 using a classifier which is not illustrated in this Figure. The sensor unit 14 is in particular configured to acquire spectral information. These may be acquired either directly, e.g., by a spectrometer, or also indirectly, e.g., by lighting the plant 18 with LEDs of different emission spectra and subsequently capturing the intensities using a RGB camera. This "scanning" of the spectrum may be performed in particular in the manner already described above. As such, it is not necessarily required that the sensor unit 14 comprises a spectrometer.

Figure 2:
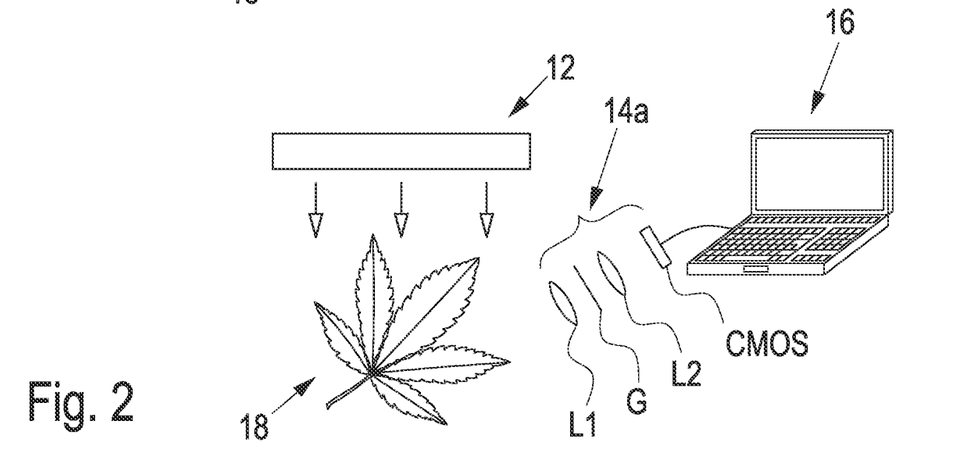
FIG. 2 is a schematic diagram of a second embodiment of the disclosure.

FIG. 2 illustrates a second embodiment of the analysis device 10 of the present disclosure. In this embodiment the sensor unit 14 is designed as a spectrometer 14a. The spectrometer 14a comprises a first lens L1, a diffraction grating G, a second lens L2, as well as a CMOS camera. The first lens L1 serves to collimate the light reflected from the plant 18. The collimated light then passes the diffraction grating G. The diffraction grating G decomposes the light into its spectral components and directs the components of different wavelengths to different regions of the CMOS camera. Thus, a spatial "spreading" of the light on the sensor surface of the CMOS camera is performed. by the subsequent evaluation of the image captured by the CMOS camera, it is therefore possible to determine the reflection spectrum of a plant 18. Optionally, in determining the reflection spectrum, information about the emission spectrum of the illumination unit 12 can be taken into consideration as well. The second lens L2 illustrated in FIG. 2 serves to again collimate the light spread by the diffraction grating G and diverging, so that the radiation arrives at the sensor surface of the CMOS camera.

Figure 3:
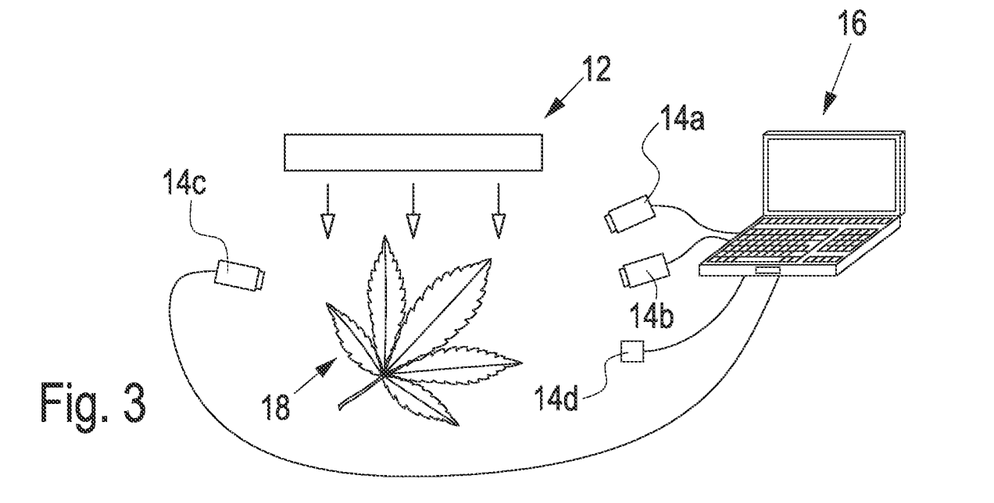
FIG. 3 is a schematic diagram of a third embodiment of the disclosure.

FIG. 3 illustrates a third embodiment of the analysis device 10 of the present disclosure. In this embodiment, the sensor unit 14 comprises a spectrometer 14a for acquiring spectral information, a first 3D camera 14b for capturing the three-dimensional contour of the plant 18, a second 3D camera 14c serving to capture the three-dimensional contour of the plant 18 from an additional perspective, and an additional sensor 14d used to acquire environmental data. According to the embodiment illustrated in FIG. 3, the first 3D camera 14b can be arranged such that it captures the three-dimensional contour of the front of the plant 18 (or the plant leaf), while the second 3D camera 14c captures the three-dimensional contour of the rear of the plant (or the plant leaf) 18. In this manner, it becomes possible to determine the volume of the plant 18 and to calculate therefrom the absolute THC concentration, for example. The additional sensor 14d may, for example, measure the air temperature in the greenhouse or in the climate chamber and provide additional information for the classifier.

Figure 4:
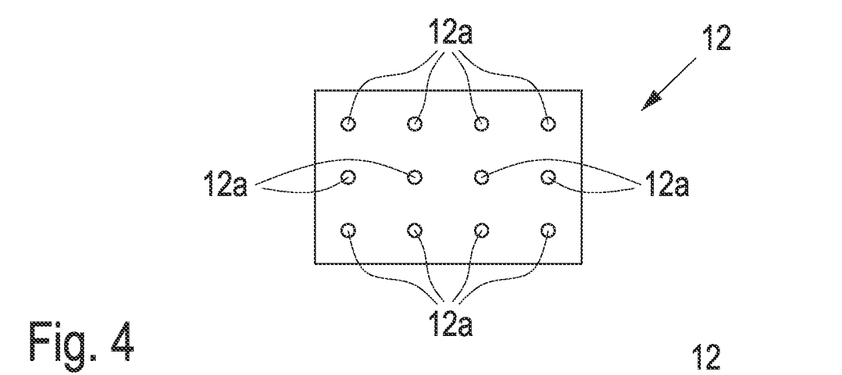
FIG. 4 is a top plan view on a first embodiment of the illumination unit of the analysis device of the present disclosure.

FIG. 4 is a top plan view on a first embodiment of the illumination unit 12. As can be seen in this Fig., the illumination unit 12 comprises a total of 12 LEDs 12a. The LEDs 12a may be identical LEDs, but may also be LEDs with different emission spectra. Here, narrowband-emitting LEDs can be used, but broadband LEDs could be used as well.

Figure 5:
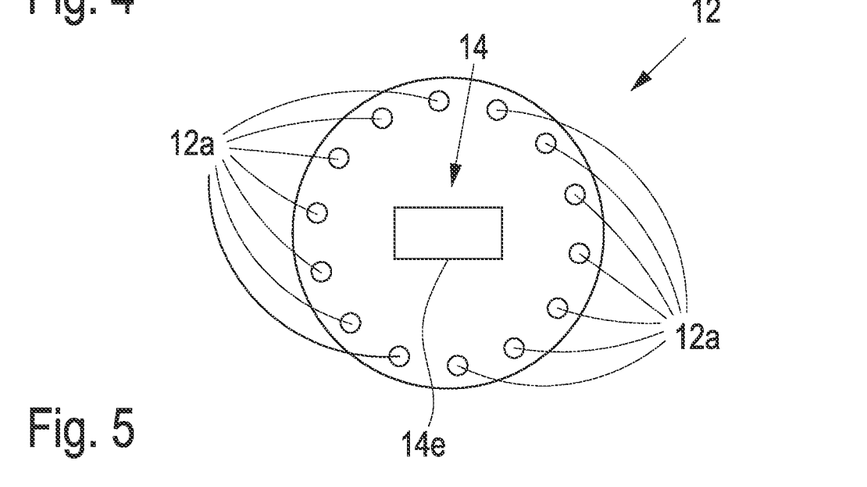
FIG. 5 is a top plan view on a second embodiment of the illumination unit of the analysis device of the present disclosure, wherein the sensor unit is integrated in the illumination unit.

FIG. 5 illustrates a top plan view on a second embodiment of the illumination unit 12. In this embodiment, the sensor unit 14, which is designed as a camera and comprises a sensor surface 14e, is integrated in the illumination unit 12. The individual LEDs 12a are arranged on a circular path surrounding the sensor surface 14e. Thereby, it is possible to achieve a particularly homogeneous illumination of the plant 18 to be analyzed, as well as a particularly advantageous luminous efficiency of the camera.

Figure 6:
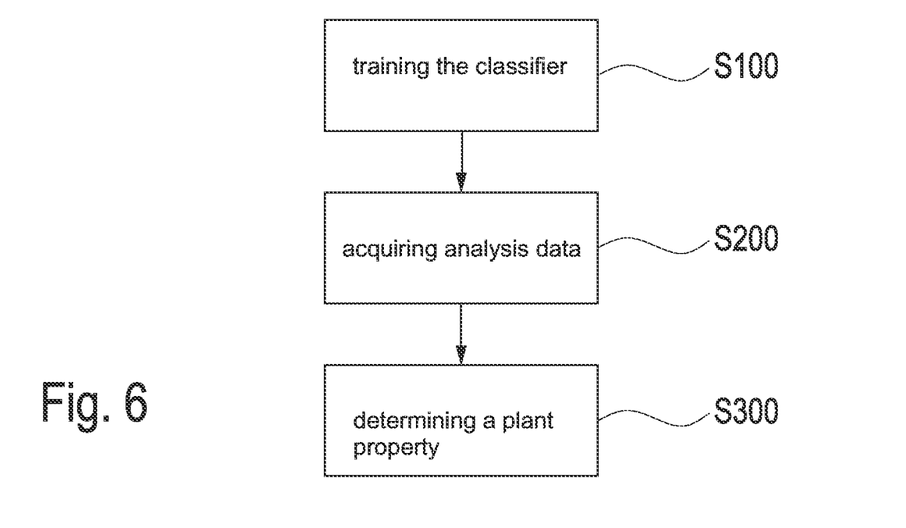
FIG. 6 is a flow diagram illustrating the method of the present disclosure.

FIG. 6 is an overview of the method of the present disclosure. First, the classifier, which is based in particular on a neural network, is trained using a training data set (step S100). This training data set includes spectral information to which specific properties of a plant 18 can be associated. For example, the classifier may learn during the training phase that an absorption peak at 350 nm indicates that the plant 18 to be analyzed is infested by a certain disease. The classifier could also learn during the training phase that measuring two absorption peaks, of which the first peak is detected at 320 nm and the second peak is detected at 480 nm, indicates that the plant is healthy and has a high water content. The classifier can also be trained to take further input data into account, in particular additional images or information about temperature, humidity, light conditions, genetic information about the plant and/or the plant varieties. The more training data is available during the training phase, the more reliable the classifier can evaluate the plant to be analyzed at a later time. After the training of the classifier (step S100), the method of the present disclosure is ready for implementation.

For the analysis of a plant 18, first, the analysis input data are acquired (step S200). The acquisition of the analysis input data is performed essentially in the same manner as the acquisition of the training input data, which will be discussed in the context of FIG. 7. As soon as the analysis input data, in particular an absorption spectrum, have been acquired, the plant property is determined (step S300) using the previously trained classifier.

Figure 7:
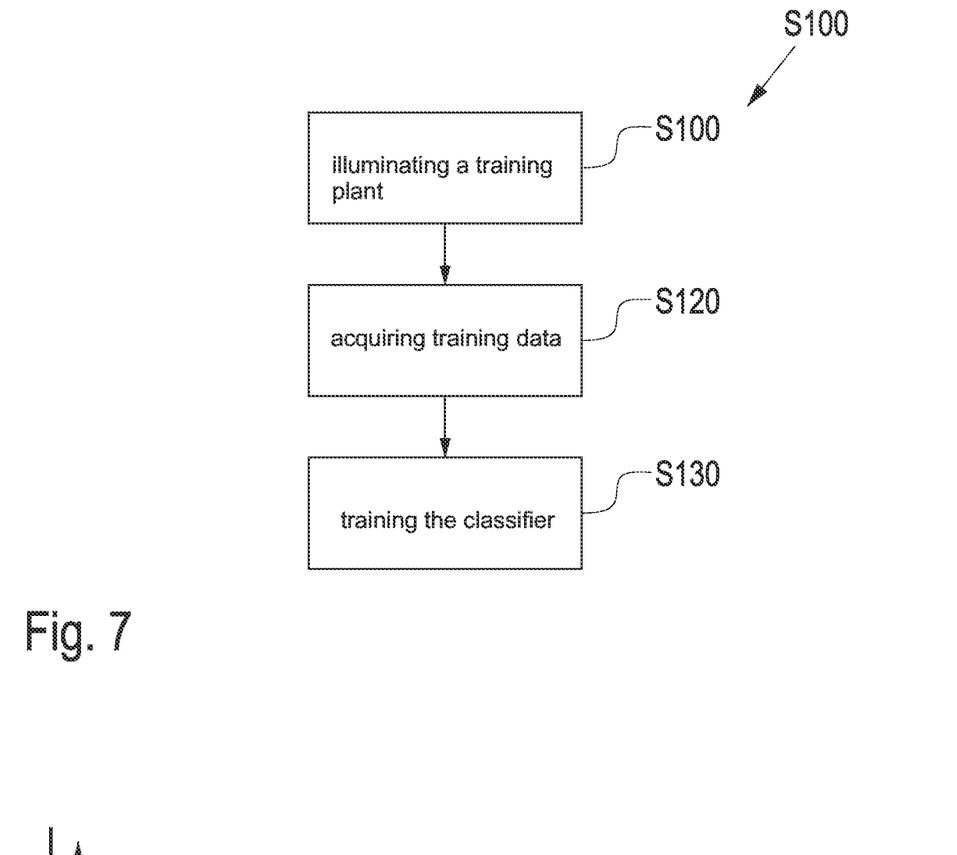
FIG. 7 is another flow diagram illustrating the individual steps of training the classifier.

FIG. 7 illustrates the individual sub-steps of the training of the classifier (step S100). First, a training plant having known properties is illuminated using the illumination unit 12 (step S110). Subsequently, the training data, specifically the training input data, are acquired by means of the sensor unit 14 (step S120). The training input data are then associated to the predetermined and already known training output data which include information about the property of a plant. In this manner, the classifier "learns" which output data or properties correlate with which input data. After the correlator has been trained (step S130), the method and the classifier are ready for implementation.

Figure 8:
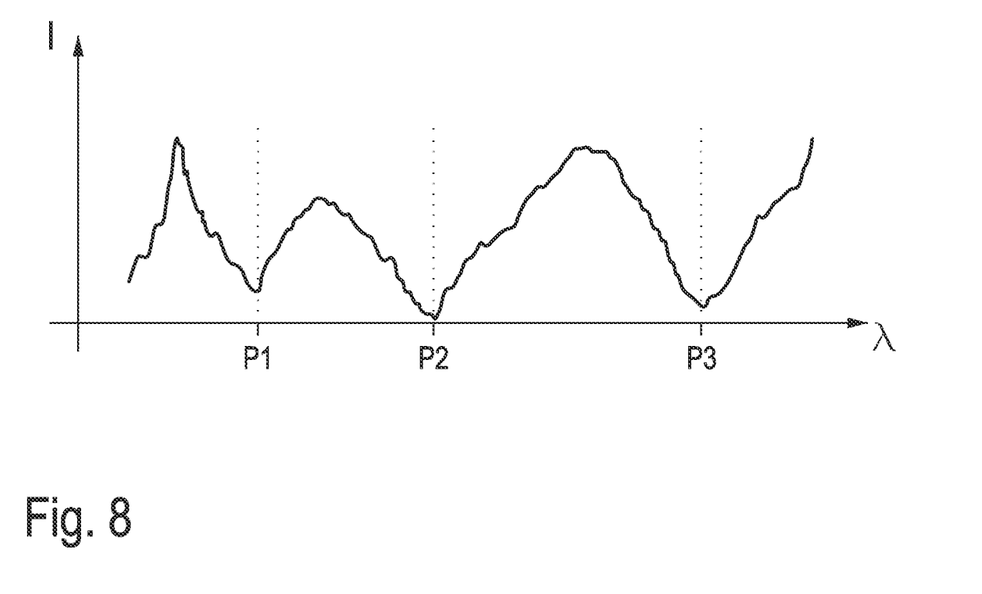
FIG. 8 is a schematic diagram of a reflection spectrum acquired.

FIG. 8 is an exemplary illustration of a reflection spectrum acquired. This reflection spectrum may have been acquired during the analysis process, for example. The reflection spectrum is the result of a spectral analysis of the light reflected from a plant. In the reflection spectrum illustrated, three different points are identified as P1, P2 and P3. These points are local minima of the reflection spectrum and local maxima of a corresponding absorption spectrum. These local extreme values may be searched for and determined in predeterminable regions, for example. It may be provided, for example, that the extreme values are determined in the wavelength ranges b1=200 to 400 nm, b2=400 to 600 nm and b3=600 to 800 nm. The result of a corresponding analysis may be, for example, that a first absorption peak is determined at P1=280 nm, a second absorption peak is determined at P2=550 nm, and a third absorption peak is determined at P3=790 nm. These three values can thus be used as analysis input data to determine that the plant analyzes is of the variety Sativa and is also healthy.

Figure 9:
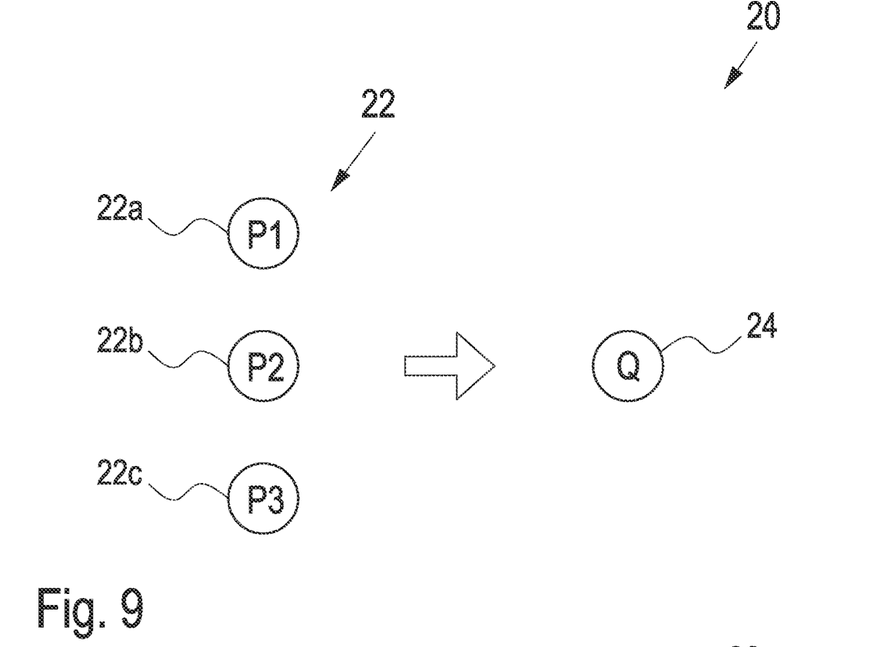
FIG. 9 is a schematic diagram of a first embodiment of the classifier.
Figure 10:
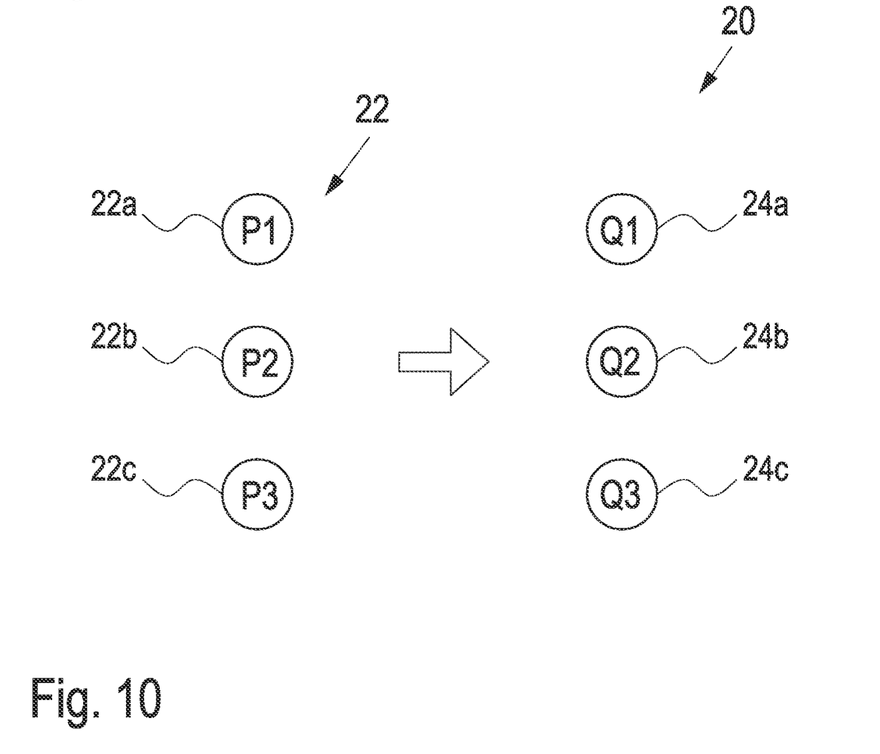
FIG. 10 is a schematic diagram of a second embodiment of the classifier.

The basic functionality of the classifiers used in the context of the disclosure is illustrated in FIGS. 9 and 10 in an abstracted manner.

FIG. 9 illustrates the case that the three features P1, P2 and P3 are determined during the analysis of a plant. As describes above, these features may be three absorption peaks, for example. In the example illustrated in FIG. 9, the features P1 to P3 are used as input data for the classifier to conclude on an output data item Q. For example, Q may relate to the state of the plant (e.g., diseased or healthy) or to the THCC concentration.

Finally, FIG. 10 illustrates the case that the three features P1, P2 and P3 are used as input data to analyze a plant, and the quantities Q1, Q2 and Q3 represent the output data. As explained in the above examples, P1 to P3 may describe three local absorption peaks. The three output quantities Q1 to Q3 may describe three properties of a plant. For example, Q1 may describe the plant variety, whereas Q2 describes the health state of a plant and Q3 describes the water content of the plant, for example.

The invention claimed is:

1. A method for analyzing a plant using an illumination unit, a sensor unit and an evaluation unit, wherein the evaluation unit comprises a data-based classifier and the method comprises the following steps:
   training the classifier, the training comprising the following steps:
   illuminating a training plant having at least one known property using the illumination unit;
   acquiring training input data by measuring the radiation reflected from the training plant;
   training of the classifier with the acquired training input data, as well as training output data, wherein the training input data at least comprises spectral information, including an absorption spectrum or a reflection spectrum of the training plant, and the training output data is associated to the training input data and comprise information about at least one property of the training plant;
   acquiring analysis input data by means of the sensor unit, wherein the acquiring comprises the following steps:
   illuminating a plant to be analyzed which has at least one unknown property, using the illumination unit;
   acquiring analysis input data by measuring the radiation reflected from the plant to be analyzed;
   determining a property of the plant to be analyzed, using the classifier previously trained with the trainings input data and the training output data and the acquired analysis input data,
   wherein
   the steps of illuminating a training plant having at least one known property using the illumination unit and acquiring training input data by measuring the radiation reflected from the training plant, comprises:
   illuminating the training plant using a first light source having a first emission spectrum;
   acquiring training input data by measuring the radiation reflected from the training plant;
   illuminating the training plant with a second light source having a second emission spectrum; and
   acquiring training input data by measuring the radiation reflected from the training plant, and wherein
   the steps of illuminating a plant to be analyzed having at least one unknown property using the illumination unit and acquiring analysis input data by measuring the radiation reflected from the plant to be analyzed include the following steps:
   illuminating the plant to be analyzed using a first light source having a first emission spectrum;
   acquiring analysis input data by measuring the radiation reflected from the plant being analyzed;
   illuminating the plant to be analyzed with a second light source having a second emission spectrum; and
   acquiring analysis input data by measuring the radiation reflected from the plant being analyzed.

2. The method according to claim 1, wherein for increasing the accuracy of the method, the training input data and the analysis input data additionally comprise images of the training plant and the plant to be analyzed.

3. The method according to claim 2, wherein the classifier additionally comprises the following steps:
   providing images as training input data which are to be used for training the classifier, and training output data associated to the images provided;
   rotating the provided images;
   associating the training output data, which are associated to the initially provided images, to the rotated images;
   combining the initially provided images and the rotated images, as well as the training output data associated to the images to an extended training data set; and
   training the classifier with the use of the extended training data set.

4. The method according to claim 1, wherein for increasing the accuracy of the method, the training input data and the analysis input data additionally include genetic information about plants.

5. The method according to claim 1, wherein the classifier is based on an artificial neural network, in particular a Convolutional Neural Network.

6. The method according to claim 1, wherein for increasing the accuracy of the method, during the training of the classifier, the training input data and the analysis input data include information about the temporal change in the input data acquired.

7. The method according to claim 1, wherein the plant is cannabis.

* * * * *